United States Patent [19]

Gottschlich et al.

[11] Patent Number: 5,532,266
[45] Date of Patent: Jul. 2, 1996

[54] ACRYLACETAMIDES

[75] Inventors: Rudolf Gottschlich, Reinheim; Karl-August Ackermann, Ober-Ramstadt; Helmut Prücher, Heppenheim; Christoph Seyfried, Seeheim; Hartmut Greiner; Gerd Bartoszyk, both of Darmstadt; Frank Mauler, Seeheim; Manfred Stohrer, Mainz; Andrew Barber, Weiterstadt, all of Germany

[73] Assignee: Merck Patent Gesellschaft mit beschrankter Haftung, Darmstadt, Germany

[21] Appl. No.: 453,811

[22] Filed: May 30, 1995

Related U.S. Application Data

[63] Continuation of Ser. No. 57,801, May 7, 1993, abandoned.

[30] Foreign Application Priority Data

May 9, 1992 [DE] Germany .................. 42 15 213.5

[51] Int. Cl.[6] .................. C07D 207/36; C07D 207/325; A61K 31/40
[52] U.S. Cl. .................. 514/428; 548/453; 548/568
[58] Field of Search .................. 514/428; 548/543, 548/568

[56] References Cited

U.S. PATENT DOCUMENTS

| | | | |
|---|---|---|---|
| 4,192,883 | 3/1980 | Cousse | 514/428 |
| 4,806,547 | 2/1989 | Giardina et al. | 514/307 |
| 5,091,392 | 2/1992 | Raddatz et al. | 546/152 |

FOREIGN PATENT DOCUMENTS

| | | |
|---|---|---|
| 2006413 | 6/1990 | Canada . |
| 2054648 | 5/1992 | Canada . |
| 330467 | 2/1989 | European Pat. Off. . |
| 2421891 | 10/1977 | France . |
| 91/08205 | 6/1991 | WIPO . |
| 91/08206 | 6/1991 | WIPO . |

OTHER PUBLICATIONS

Barber et al., "A pharmacological profile of the novel, peripherally-selective κ-opioid . . . ", Br. J. Pharmacol (1994), 113, pp. 1317–1327.

Tarayre, et al., *Arzneim–Forsch./Drug Res.*, 33(II), No. 7, pp. 931–935, 1983.

Hendrickson et al, *Organic Chemistry*, 3rd Edition, p. 513, 1970.

CA78(9) 58099r, Clemence et al, FR 2113786 patent abstract, Aug. 1972.

CA77(11) 75024; Clemence et al, DE 2155906 patent abstract, May 1972.

*Primary Examiner*—C. Warren Ivy
*Assistant Examiner*—D. Margaret M. Mach
*Attorney, Agent, or Firm*—Millen, White, Zelano, & Branigan

[57] ABSTRACT

Novel arylacetamides of the formula I $$Q-CO-\underset{\underset{R^3}{|}}{\overset{\overset{R^1}{|}}{C}}-R^2 \quad \text{I}$$

in which

Q is $R^4$—CH(CH$_2$Z)—NA—,

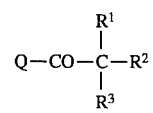

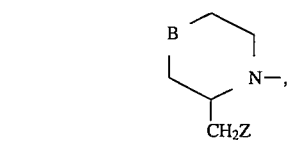 or 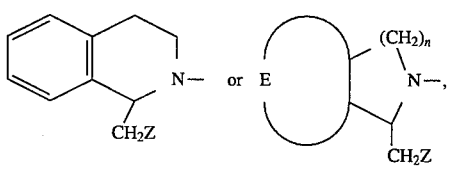

$R^1$ is Ar, cycloalkyl with 3–7 C atoms or $C_4$–$C_8$-cycloalkyl-$C_1$–$C_7$-alkyl, $R^2$ is Ar, $R^3$ is H, OH, OA or A, $R^4$ is A or phenyl which can optionally be substituted once or twice by F, Cl, Br, I, OH, OA, CF$_3$, NO$_2$, NH$_2$, NHA, NHCOA, NHSO$_2$A or NA$_2$, $R^5$ and $R^6$ are each, independently of one another, H, F, Cl, Br, I, OH, OA, CF$_3$, NH$_2$, NHA, NA$_2$, NHCOA, NHCONH$_2$, NO$_2$ or taken together are methylenedioxy, A is alkyl with 1–7 C atoms, and physiologically acceptable salts thereof.

22 Claims, No Drawings

ACRYLACETAMIDES

This application is a continuation of application Ser. No. 08/057,801, filed May 7, 1993 now abandoned.

BACKGROUND OF THE INVENTION

The invention is directed to novel arylacetamides used as pharmaceutical agents in human and veterinary medicines, particularly for providing an analgesic effect and/or neuroprotective effect.

Similar compounds are described in DE-A1 39 35 371 which is incorporated herein by reference.

SUMMARY OF THE INVENTION

The invention relates to novel acrylacetamides of the formula I

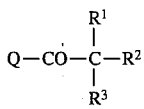

in which

Q is $R^4$—CH(CH$_2$Z)—NA—,

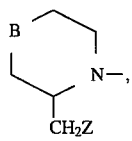

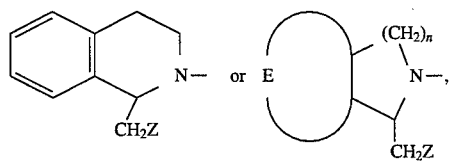

$R^1$ is Ar, cycloalkyl with 3–7 C atoms or $C_4$–$C_8$-cycloalkyl-$C_1$–$C_7$-alkyl, $R^2$ is Ar, $R^1$ and $R^2$ together may also be

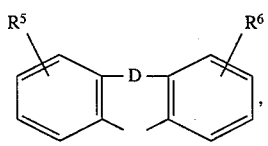

$R^3$ is H, OH, OA or A, $R^4$ is A or phenyl which can optionally be substituted once or twice by F, Cl, Br, I, OH, OA, CF$_3$, NO$_2$, NH$_2$, NHA, NHCOA, NHSO$_2$A or NA$_2$, $R^5$ and $R^6$ are each, independently of one another, H, F, Cl, Br, I, OH, OA, CF$_3$, NH$_2$, NHA, NA$_2$, NHCOA, NHCONH$_2$, NO$_2$ or taken together are methylenedioxy, A is alkyl with 1–7 C atoms, B is CH$_2$, O, NH, NA, N—COA, N—COOA or a bond, E is a fused-on ring system, preferably a single fused-on ring, having up to three unsaturated bonds, where one C atom can optionally be replaced by S, N or O, and which can optionally be substituted once or twice by F, Cl, Br, I, OH, OA, NH$_2$, NHA, NA$_2$, NH—COA, NA—COA or NH—CONH$_2$, D is CH$_2$, O, S, NH, NA, —CH$_2$—CH$_2$—, —CH=CH—, —CH$_2$O—, —CH$_2$NH—, —CH$_2$NA— or a bond, Z is 1-pyrrolidinyl which can optionally be substituted once by OH, OA, O—COCH$_3$ or CH$_2$OH, Ar is a mono- or bicyclic aromatic radical which can optionally be substituted once, twice or three times by A, Hal, OH, OA, CF$_3$, NH$_2$, NHA, NA$_2$, NHCOA and/or NHCONH$_2$, and n is 1 or 2 and the salts thereof.

It was the object of the invention to find novel compounds with valuable properties, especially those which can be used for the preparation of medicaments.

DETAILED DESCRIPTION OF THE INVENTION

It has been found that the compounds of the formula I and their physiologically compatible salts possess valuable pharmacological properties. They exhibit an analgesic action and antagonize inflammation-related hyperalgesia in particular. Thus, the compounds are effective in the writhing test on mice or rats (for method, see Siegmund et al., *Proc. Soc. Exp. Biol.* 95, (1957), 729–731). The analgesic action can also be demonstrated in the tail flick test on mice or rats (for methodology, see d'Amour and Smith, *J. Pharmacol. Exp. Ther.* 72 (1941), 74–79) and in the hot plate test (see Schmauss and Yaksh, *J. Pharmacol. Exp. Ther.* 228 (1984), 1–12, and the literature cited therein). Especially potent actions are to be observed in rats in the model of carrageenin-induced hyperalgesia (see Batoszyk and Wild, *Neuroscience Letters* 101 (1989) 95). In these tests, the compounds show little or no tendency to cause physical dependence. Furthermore, antiinflammatory, antiasthmatic, diuretic, anticonvulsant, neuroprotective and/or antitussive actions can also be demonstrated by methods commonly used for this purpose. The compounds show a high affinity with respect to the binding behavior to kappa receptors. They are, moreover, suitable for protecting against and treating cerebral oedemas and states of blood and oxygen supply deficiency of the central nervous system, especially hypoxia.

The compounds can therefore be used as pharmacologically active ingredients in human and veterinary medicine. They are also suitable as intermediates for the preparation of other compounds with valuable properties.

The invention relates to compounds of the formula I and to their salts.

The group A is alkyl with 1, 2, 3, 4, 5, 6 or 7 C atoms, especially methyl or ethyl, but also propyl, isopropyl, butyl, isobutyl, sec-butyl or tert-butyl. Accordingly, the group OA is preferably methoxy or ethoxy, furthermore propoxy, isopropoxy, butoxy, isobutoxy, sec-butoxy or tert-butoxy, and the group —NA— is preferably N-methyl, the group —NHA is methyl-NH and the group —NA$_2$ is N,N-dimethylamino.

Accordingly, the groups shown below have the preferred meanings specified as follows:

—NH—CO—A: acetamido, propionamido;

—NA—CO—A: N-methylacetamido, N-methylpropionamido.

Ar is preferably unsubstituted phenyl, also preferably o-, m- or p-aminophenyl, furthermore preferably o-, m- or p-hydroxyphenyl, o-, m- or p-acetamidophenyl, o-, m- or p-fluorophenyl, o-, m- or p-chlorophenyl, o-, m- or p-trifluoromethylphenyl. Among the substituted phenyl radicals, those in the p position but also those in the m position are preferred.

The $C_1$–$C_7$ alkyl group in the $C_4$–$C_8$-cycloalkyl-$C_1$–$C_7$-alkyl group of $R_1$ is preferably —$CH_2$— or —$CH_2$—$CH_2$—

$R^1$ and $R^2$ are each, independently of one another, particularly preferably phenyl, and furthermore p-fluorophenyl or p-chlorophenyl.

Likewise, $R^1$ and $R^2$ can also preferably be connected together via their ortho positions by a direct linkage or via an O bridge or a methylene bridge.

$R_3$ is particularly preferably H or OH, furthermore OA or methyl.

$R_4$ is preferably phenyl, p-hydroxyphenyl, p-methoxyphenyl, also p-F-, p-Cl- or p-trifluoromethylphenyl, but also alkyl such as, for example, methyl, ethyl, propyl, isopropyl, butyl, isobutyl, sec-butyl, tert-butyl or pentyl.

$R^5$ and $R^6$ are preferably each, independently of one another, hydrogen, F or Cl, also OH or methoxy.

The radical Q preferably has the following meanings:

N-methyl-N-(1-phenyl-2-pyrrolidinoethyl)amino;

N-methyl-N-[1-phenyl-2-(3-hydroxypyrrolidino)ethyl]amino;

N-methyl-N-(1-p-hydroxyphenyl-2-pyrrolidinoethyl)amino;

N-methyl-N-[1-p-hydroxyphenyl-2-(3-hydroxypyrrolidino)ethyl]amino;

N-methyl-N-[1-(p-methoxyphenyl)-2-pyrrolidinoethyl]amino;

N-methyl-N-[1-(p-methoxyphenyl)-2-(3-hydroxypyrrolidino)ethyl]amino;

N-methyl-N-(2-pyrrolidino-3-methylbutyl)amino;

N-methyl-N-[2-(3-hydroxypyrrolidino)-3-methylbutyl]amino;

N-methyl-N-(2-pyrrolidino-4-methylpentyl)amino;

N-methyl-N-[2-(3-hydroxypyrrolidino)-4-methylpentyl]amino;

2-(pyrrolidinomethyl)piperidino;

2-(3-hydroxypyrrolidinomethyl)piperidino;

2-(pyrrolidinomethyl)-4-ethoxycarbonylpiperazino;

2-(3-hydroxypyrrolidinomethyl)-4-ethoxycarbonylpiperazino;

2-(pyrrolidinomethyl)-1,2,3,4-tetrahydroisoquinolin-1-yl;

2-(3-hydroxypyrrolidinomethyl)-1,2,3,4-tetrahydroisoquinolin-1-yl;

2-(pyrrolidinomethyl)pyrrolidino or 2-(3-hydroxypyrrolidinomethyl) pyrrolidino.

Z is pyrrolidino which is preferably unsubstituted or substituted by OH in position 3; but can furthermore also be substituted by OA, —O—$COCH_3$ or —$CH_2OH$.

Accordingly, the invention particularly relates to those compounds of the formula I in which at least one of the said radicals has one of the preferred meanings indicated above. Some preferred groups of compounds can be expressed by the following formulae Ia to Ih, which correspond to formula I and in which the radicals not identified precisely have the meaning indicated for formula I but in which in Ia $R^1$ and $R^2$ are each phenyl;

in Ib $R^1$ and $R^2$ are each p-fluoro- or p-chlorophenyl;

in Ic $R^1$ and $R^2$ are each phenyl and $R^3$ is H;

in Id $R^1$ and $R^2$ are each phenyl and $R^3$ is methyl;

in Ie $R^1$ and $R^2$ are each p-fluoro- or p-chlorophenyl and $R^3$ is H;

in If $R^1$ and $R^2$ together are

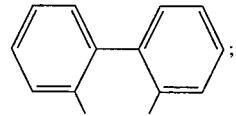

in Ig $R^1$ and $R^2$ together are

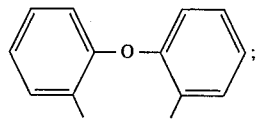

in Ih $R^1$ and $R^2$ together have the meaning indicated in If or Ig, and $R^3$ is H.

Further preferred compounds are those of the formulae I' and Ia' to Ih' which correspond to the formulae I and Ia to Ih, respectively, but in which Q is additionally in each case (a) N-methyl-N-(1-phenyl-2-pyrrolidinoethyl)amino;

(b) N-methyl-N-[1-phenyl-2-(3-hydroxypyrrolidino)ethyl]amino;

(c) N-methyl-N-[1-(p-hydroxyphenyl)-2-pyrrolidinoethyl]amino;

(d) N-methyl-N-[1-(p-hydroxyphenyl)-2-(3-hydroxypyrrolidino)ethyl]amino;

(e) N-methyl-N-[1-(p-methoxyphenyl)-2-pyrrolidinoethyl]amino;

(f) N-methyl-N-[1-(p-methoxyphenyl)-2-(3-hydroxypyrrolidino)ethyl]amino;

(g) N-methyl-N-(2-pyrrolidino-3-methylbutyl)amino;

(h) N-methyl-N-[2-(3-hydroxypyrrolidino)-3-methylbutyl]amino;

(i) N-methyl-N-(2-pyrrolidino-4-methylpentyl)amino;

(k) N-methyl-N-[2-(3-hydroxypyrrolidino)-4-methylpentyl]amino;

(l) 2-(pyrrolidinomethyl)piperidino;

(m) 2-(3-hydroxypyrrolidinomethyl)piperidino;

(n) 2-(pyrrolidinomethyl)-4-ethoxycarbonylpiperazino;

(o) 2-(3-hydroxypyrrolidinomethyl)-4-ethoxycarbonylpiperazino;

(p) 2-(pyrrolidinomethyl)-1,2,3,4-tetrahydroisoquinolin-1-yl;

(q) 2-(3-hydroxypyrrolidinomethyl)-1,2,3,4-tetrahydroisoquinolin-1-yl;

(r) 2-(pyrrolidinomethyl)pyrrolidino or (s) 2-(3-hydroxypyrrolidinomethyl)pyrrolidino.

The invention furthermore relates to a process for the preparation of arylacetamides of the formula I according to claim 1, and the salts thereof, characterized in that a compound of the formula II $$Q-H \qquad\qquad II$$

in which Q has the meaning stated for formula I, is reacted with a compound of the formula III

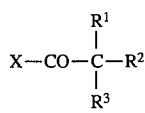

in which
X is Cl, Br, OH, OA, NH, —N₃, acyloxy, Ar-alkoxy with 7–11 C atoms or aroyloxy with 6–10 C atoms, particularly Ar—CO—O, wherein Ar is as defined above, and $R^1$, $R^2$ and $R^3$ have the meanings stated for formula I or in that a radical Q, $R^1$, $R^2$ and/or $R^3$ in a compound of the formula I is converted into another radical Q, $R^1$, $R^2$ and/or $R_3$, or in that a compound which otherwise corresponds to formula I but which, in place of one or more hydrogen atoms, contains one or more solvolyzable group(s) is treated with a sovolyzing agent, and/or in that a basic compound of the formula I is converted by treatment with an acid into one of its salts.

The compounds of the formula I are normally prepared by methods known per se, as described in the literature (e.g., in the standard works such as Houben-Weyl, Methoden der Organischen Chemie (Methods of Organic Chemistry), Georg-Thieme-Verlag, Stuttgart), i.e., under reaction conditions which are known and suitable for said reactions. It is also possible to use variants which are known per se and are not mentioned in further detail here.

The starting materials are generally known or can be prepared analogously to known substances by processes known per se. If desired, they can also be formed in situ in a manner such that they are not isolated from the reaction mixture, but immediately reacted further to give the compounds of the formula I. On the other hand, the reaction can be carried out in steps, in which case it is possible to isolate other intermediates.

The individual process variants are illustrated in further detail below.

The compounds of the formula I can preferably be prepared by reacting the compounds of the formula II with carboxylic acids of the formula III or their functional derivatives. Suitable functional derivatives of the compounds of the formula III are especially the corresponding esters, in particular the methyl or ethyl esters, and the halides, anhydrides or azides; the chlorides are preferred.

Compounds of the formula II can be obtained, for example, by reaction of 1-(chloromethyl)-1,2,3,4-tetrahydroisoquinoline with pyrrolidine or 3-hydroxypyrrolidinoethane, of 1-amino-1-phenyl-2-pyrrolidinoethane with methyl iodide, of 1-N-methylamino-1-phenyl-2-halogenoethane (halogen is preferably Cl or Br) with pyrrolidine or 3-hydroxypyrrolidine or of 1-halogeno-2-N-methylamino-4-methylpentane with pyrrolidine or its 3-hydroxy derivative.

Compounds of the formula II can furthermore be obtained by reaction of 2-halogenomethyl derivatives of piperazine or piperidine with pyrrolidine or 3-hydroxypyrrolidine.

Examples of typical compounds of the formula III are diphenylacetyl chloride, bromide and azide, methyl and ethyl diphenylacetates, diphenylacetic anhydride, diphenylacetonitrile and the corresponding derivatives of di(p-Cl-phenyl)- and di(p-F-phenyl)-acetic acid and the corresponding derivatives of hydroxydiphenylacetic acid and of 2,2-diphenylpropionic acid.

Reaction of II with III or III derivatives preferably takes place in the presence or absence of an inert organic solvent, for example of a halogenated hydrocarbon such as dichloromethane, chloroform or trichloroethene, of an alcohol such as methanol, ethanol or butanol, of an ether such as tetrahydrofuran (THF) or dioxane, of an amide such as dimethylformamide (DMF), of a sulfoxide such as dimethyl sulfoxide (DMSO) and/or in the presence or absence of a condensing agent, for example a base, at temperatures between −20° and 200°, preferably 0° and 100°. Examples of suitable bases are alkali metal hydroxides such as NaOH or KOH, alkali metal carbonates such as $Na_2CO_3$ or $K_2CO_3$, tertiary amines such as triethylamine or pyridine. Particularly preferred as solvent is dichloromethane and as base is triethylamine.

It is furthermore possible in a compound of the formula I to convert one or more of the radicals Q, $R^1$, $R^2$ and/or $R^3$ into one or more other radicals Q, $R^1$, $R^2$ and/or $R^3$.

Thus, ether groups (for example OA groups) can be cleaved to form OH groups, for example, by treatment with dimethyl sulfide/boron tribromide complex, for example in toluene, THF or DMSO, or by fusion with pyridine hydrohalides or aniline hydrohalides, preferably pyridine hydrochloride, at about 150°–250°, or by treatment with diisobutylaluminium hydride in toluene at about 0°–110°.

It is furthermore possible to etherify OH groups, for example by initially preparing the corresponding alkali metal (for example Na or K) alcoholates, phenolates or salts, and reacting the latter with appropriate halogen compounds, for example with alkyl halides such as methyl chloride, bromide or iodide, chloro- or bromo-acetamide, expediently in the presence of one of the abovementioned solvents at temperatures between 0° and 100°.

Nitro groups can be reduced to amino groups, preferably by catalytic hydrogenation under the abovementioned conditions, for example with Raney Ni in methanol or ethanol at 15°–40° under atmospheric pressure.

Amino groups can be acylated, for example with acid chlorides such as acetyl or methanesulfonyl chloride, or the monoester chloride of oxalic acid or succinic acid, preferably in inert solvents such as dichloromethane at 15°–40°.

It is furthermore possible to alkylate amino groups by methods known per se.

A base of the formula I can furthermore be converted with an acid into the relevant acid addition salt. Suitable acids for this reaction are those which provide physiologically acceptable salts. Thus, it is possible to use inorganic acids, for example sulfuric acid, nitric acid, hydrohalic acids such as hydrochloric acid or hydrobromic acid, phosphoric acids such as orthophosphoric acid, sulfamic acid, as well as organic acids, especially aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid., lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemonosulfonic and naphthalenedisulfonic acids and lauryl sulfuric acid. Salts with physiologically unacceptable acids, for example picrates, can be used to purify the compounds of the formula I.

If desired, the free bases of formula I can be liberated from their salts by treatment with strong bases such as sodium or potassium hydroxide or sodium or potassium carbonate.

The compounds of the formula I contain one or more chiral centers and can therefore exist in racemic or optically active form. Racemates obtained can be mechanically or chemically resolved into the enantiomers by methods known per se. Preferably, diastereomers are formed from the racemic mixture by reaction with an optically active resolving agent. Examples of suitable resolving agents are optically active acids such as the D and L forms of tartaric acid, diacetyltartaric acid, dibenzoyltartaric acid, mandelic acid, malic acid or lactic acid, or the various optically active camphorsulfonic acids such as β-camphorsulfonic acid.

It is also advantageous to resolve enantiomers using a column packed with an optically active resolving agent (for example dinitrobenzoylphenylglycine); an example of a suitable mobile phase is a hexane/isopropanol/acetonitrile mixture, for example in the ratio 82:15:3 by volume.

It is, of course, also possible to obtain optically active compounds of the formula I by the methods described above by use of starting materials (for example those of the formula II) which are already optically active.

The invention furthermore relates to the use of the compounds of the formula I and of their physiologically acceptable salts for the production of pharmaceutical preparations, in particular by non-chemical means. For this they can be converted together with at least one solid, liquid and/or semiliquid vehicle or ancillary substance and, where appropriate, in combination with one or more other active ingredients into a suitable dosage form.

The invention furthermore relates to compositions, in particular pharmaceutical preparations, which contain at least one compound of the formula I and/or one of its physiologically acceptable salts.

These preparations can be used as medicaments in human or veterinary medicine. Suitable vehicles are organic or inorganic substances which are suitable for enteral (for example oral), parenteral or topical administration and which do not react with the novel compounds, for example water, vegetable oils, benzyl alcohols, alkylene glycols, polyethylene glycols, glycerol triacetate, gelatin, carbohydrates such as lactose or starch, magnesium stearate, talc and petrolatum. Forms used for oral administration are, in particular, tablets, pills, coated tablets, capsules, powders, granules, syrups, juices or drops, forms used for rectal administration are suppositories, forms used for parenteral administration are solutions, preferably oily or aqueous solutions, as well as suspensions, emulsions or implants, and forms used for topical administration are ointments, creams or powders. The novel compounds can also be lyophilized and the resulting lyophilizates be used, for example, for preparing products for injection. The indicated preparations can be sterilized and/or contain ancillary substances such as lubricants, preservatives, stabilizers and/or wetting agents, emulsifiers, salts to influence the osmotic pressure, buffer substances, colorants, flavorings and/or aromatizing substances. They can, if required, also contain one or more other active ingredients, for example, one or more vitamins.

The compounds of the formula I and their physiologically acceptable salts can be used for controlling diseases, especially states of pain, but also for reducing the secondary damage after ischaemia.

The substances of the invention are normally administered analogously to known analgesics, for example, IBUPROFEN or DICLOFENAC, in an amount effective to produce an analgesic effect, preferably in dosages of between about 1 and 500 mg, especially of between 5 and 100 mg, per dosage unit. The daily dosage is preferably between about 0.02 and 10 mg/kg of body weight. However, the particular dose for each individual patient depends on a very wide variety of factors, for example efficacy of the particular compound used, age, body weight, general state of health, sex, diet, time and route of administration, rate of excretion, drug combination and severity of the particular disease for which the therapy is intended. Oral administration is preferred.

All temperatures are given in °C. hereinbefore and hereinafter. The compounds of the formula I tend to decompose on heating so that no clear melting points can be determined and, as a substitute for this, the corresponding $R_f$ values (thin-layer chromatography) are given. In the following examples, "usual working up" means: water or dilute sodium hydroxide solution is added if necessary, the mixture is extracted with dichloromethane, the organic phase is separated off, dried with sodium sulfate, filtered and evaporated, and purification is by chromatography on silica gel and/or by crystallization.

HCl'=hydrochloride. Rf=rf on thin-lay silica gel 60 $F_{254}$ (E. Merck, Cat. No. 5715), $CH_2Cl_2/CH_3OH$ 9:1 $[\alpha]=[\alpha]_D^{20}$, c=1 in methanol.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. de In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application German P 42 15 213.5, filed May 9, 1992, are hereby incorporated by reference.

EXAMPLES

Example 1

2.2 g of (1S)-1-methylamino-1-phenyl-2-((3S)-3-hydroxypyroolidino)ethane [obtainable from (1S)-1-amino-1-phenyl-2-chloroethane by reaction with (3S)-3-hydroxypyrrolidine and subsequent methylation with methyl iodide] dissolved in 20 ml of THF are added dropwise to a solution of 2.3 g of diphenylacetyl chloride in 100 ml of THF at room temperature, and the mixture is stirred for 10 minutes. The usual working up results in N-methyl-N-[(1S)-1-phenyl-2-((3S)-3-hydroxypyrrolidino) ethyl]-2,2-diphenylacetamide, Rf: 0.60.

The following are obtained analogously by reaction of diphenylacetyl chloride with (1S)-1-methylamino-1-(p-methoxyphenyl)-2-((3S)-3-hydroxypyrrolidino)ethane:

N-methyl-N-[(1S)-1-(p-methoxyphenyl)-2-((3S)-3-hydroxypyrrolidino)ethyl]-2,2-diphenylacetamide, Rf: 0.61;

with (1S)-1-methylamino-1-phenyl-2-pyrrolidinoethane:

N-methyl-N-[(1S)-1-phenyl-2-pyrrolidinoethyl]-2,2-diphenylacetamide, Rf: 0.71;

with (1S)-1-methylamino-1-(o-methoxyphenyl)-2-((3S)-3-hydroxypyrrolidino)ethane:

N-methyl-N-[(1S)-1-(o-methoxyphenyl)-2-((3S)-3-hydroxypyrrolidino)ethyl]-2,2-diphenylacetamide;

with 1-(pyrrolidinomethyl)-1,2,3,4-tetrahyydroisoquinoline:

2-diphenylacetyl-1- (pyrrolidinomethyl) -1,2,3,4-tetrahydroisoquinoline, Rf: 0.50;

with 2-(pyrrolidinomethyl) pyrrolidine:

(2S)-1-diphenylacetyl-2-(pyrrolidinomethyl)pyrrolidine, Rf: 0.20;

with N-methyl-N-(2-pyrrolidino-4-methylpentyl)amine:

N-methyl-N-(2-pyrrolidino-4-methylpentyl)-2,2-diphenylacetamide, Rf: 0.61;

with N-methyl-N-[2-((3S)-hydroxypyrrolidino)-4-methylpentyl]amine;

N-methyl-N-[2-((3S)-hydroxypyrrolidino)-4-methylpentyl]-2,2-diphenylacetamide, Rf: 0.64;

with N-methyl-N-(2-pyrrolidino-3-methylbutyl)amine;

N-methyl-N-(2-pyrrolidino-3-methylbutyl)-2,2-diphenylacetamide;

with N-methyl-N-[2-((3S)-hydroxypyrrolidino)-3-methylbutyl]amine:

N-methyl-N-[2-((3S)-hydroxypyrrolidino)-3-methylbutyl]-2,2-diphenylacetamide;

with (1S)-1-methylamino-1-(p-hydroxyphenyl)-2-((3S)-3-hydroxypyrrolidino)ethane:

N-methyl-N-[(1S)-1-(p-hydroxyphenyl)-2-((3S)-3-hydroxypyrrolidino)ethyl]-2,2-diphenylacetamide;

with (1S)-1-methylamino-1-(p-chlorophenyl)-2-pyrrolidinoethane:

N-methyl-N-[(1S)-1-(p-chlorophenyl)-2-pyrrolidinoethyl]-2,2-diphenylacetamide;

with 1-((3S)-3-hydroxypyrrolidinomethyl)-1,2,3,4-tetrahydroisoquinoline:

2-diphenylacetyl-1-((3S)-3-hydroxypyrrolidinomethyl)-1,2,3,4-tetrahydroisoquinoline;

with (1S)-1-methylamino-1-(2,4-dimethoxyphenyl)-2-((3S)-3-hydroxypyrrolidino)ethane:

N-methyl-N-[(1S)-1-(2,4-dimethoxyphenyl)-2-((3S)-3-hydroxypyrrolidino)ethyl]-2,2-diphenylacetamide;

with (1S)-1-methylamino-1-(p-trifluoromethylphenyl)-2-((3S)-3-hydroxypyrrolidino)ethane:

N-methyl-N-[(1S)-1-(p-trifluoromethylphenyl)-2-((3S)-3-hydroxypyrrolidino)ethyl]-2,2diphenylacetamide;

with (1S)-1-methylamino-1-(p-methylphenyl)-2-((3S)-3-hydroxypyrrolidino)ethane:

N-methyl-N-[(1S)-1-(p-methylphenyl)-2-((3S)-3-hydroxypyrrolidino)ethyl]-2,2-diphenylacetamide;

with (1S)-1-methylamino-1-(p-aminophenyl)-2-((3S)-3-hydroxypyrrolidino)ethane:

N-methyl-N-[(1S)-1-(p-aminophenyl)-2-((3S)-3-hydroxypyrrolidino)ethyl]-2,2-diphenylacetamide;

with (1S)-1-methylamino-1-(p-fluorophenyl)-2-((3S)-3-hydroxypyrrolidino)ethane:

N-methyl-N-[(1S)-1-(p-fluorophenyl)-2-((3S)-3hydroxypyrrolidino)ethyl]-2,2-diphenylacetamide;

with (1S)-1-methylamino-1-(2,4-difluorophenyl)-2-((3S)-3-hydroxypyrrolidino)ethane:

N-methyl-N-[(1S)-1-(2,4-difluorophenyl)-2-((3S)-3-hydroxypyrrolidino)ethyl]-2,2-diphenylacetamide.

Example 2

The following are obtained in analogy to Example 1 by reaction of bis(p-fluorophenyl)acetic acid with (1S)-1-methylamino-1-phenyl-2-((3S)-3-hydroxypyrrolidino)ethane:

N-methyl-N-[(1S)-1-phenyl-2-((3S)-3-hydroxypyrrolidino)ethyl]-2,2-bis(p-fluorophenyl)acetamide;

with (1S)-1-methylamino-1-(p-methoxyphenyl)-2-((3S)-3-hydroxypyrrolidino)ethane:

N-methyl-N-[(1S)-1-(p-methoxyphenyl)-2-((3S)-3-hydroxypyrrolidino)ethyl]-2,2-bis(p-fluorophenyl)acetamide;

with (1S)-1-methylamino-1-phenyl-2-pyrrolidinoethane:

N-methyl-N-[(1S)-1-phenyl-2-pyrrolidinoethyl]-2,2-bis(p-fluorophenyl)acetamide;

with (1S)-1-methylamino-1-(p-methoxyphenyl)-2-((3S)-3-hydroxypyrrolidino)ethane:

N-methyl-N-[(1S)-1-(p-methoxyphenyl)-2-((3S)-3-hydroxypyrrolidino)ethyl]-2,2-bis(p-fluorophenyl) acetamide;

with 1-(pyrrolidinomethyl)-1,2,3,4-tetrahydroisoquinoline:

2-bis(p-fluorophenyl)acetyl-1-(pyrrolidinomethyl)-1,2,3,4-tetrahydroisoquinoline;

with 2-(pyrrolidinomethyl)pyrrolidine:

(2S)-1-bis(p-fluorophenyl)acetyl-2-(pyrrolidinomethyl)pyrrolidine;

with N-methyl-N-(2-pyrrolidino-4-methylpentyl)amine:

N-methyl-N-(2-pyrrolidino-4-methylpentyl)-2,2-bis(p-fluorophenyl)acetamide;

with N-methyl-N-[2-((3S)-hydroxypyrrolidino)-4-methylpentyl]amine:

N-methyl-N-[2-((3S)-hydroxypyrrolidino)-4-methylpentyl]-2,2-bis(p-fluorophenyl)acetamide;

with N-methyl-N-(2-pyrrolidino-3-methylbutyl)amine:

N-methyl-N-(2-pyrrolidino-3-methylbutyl)-2,2-bis(p-fluorophenyl)acetamide;

with N-methyl-N-[2-((3S)-hydroxypyrrolidino)-3-methylbutyl]amine:

N-methyl-N-[2-((3S)-hydroxypyrrolidino)-3-methylbutyl]-2,2-bis(p-fluorophenyl)acetamide;

with (1S)-1-methylamino-1-(p-hydroxyphenyl)-2-((3S)-3hydroxypyrrolidino)ethane:

N-methyl-N-[(1S)-1-(p-hydroxyphenyl)-2-((3S)-3-hydroxypyrrolidino)ethyl]-2,2-bis(p-fluorophenyl-acetamide;

with (1S)-1-methylamino-1-(p-chlorophenyl)-2-pyrrolidinoethane:

N-methyl-N-[(1S)-1-(p-chlorophenyl)-2-pyrrolidinoethyl]-2,2-bis(p-fluorophenyl)acetamide;

with 1-((3S)-3-hydroxypyrrolidinomethyl)-1,2,3,4-tetrahydroisoquinoline:

2-[bis(p-fluorophenyl)acetyl]-1-((3S)-3-hydroxypyrrolidinomethyl)-1,2,3,4-tetrahydroisoquinoline;

with (1S)-1-methylamino-1-(2,4-dimethoxyphenyl)-2-((3S)-3-hydroxypyrrolidino)ethane:

N-methyl-N-[(1S)-1-(2,4-dimethoxyphenyl)-2-((3S)-3-hydroxypyrrolidino)ethyl]-2,2 -bis(p-fluorophenyl)acetamide with (1S)-1-methylamino-1-(2,4-dimethoxyphenyl)-2-pyrrolidinoethane:

N-methyl-N-[(1S)-1-(2,4-dimethoxyphenyl)-2-pyrrolidinoethyl]-2,2-bis(p-fluorophenyl)acetamide;

with (1S)-1-methylamino-1-(p-trifluoromethylphenyl)-2-((3S)-3-hydroxypyrrolidino)ethane:

N-methyl-N-[(1S)-1-(p-trifluoromethylphenyl)-2-((3S)-3-hydroxypyrrolidino)ethyl]-2,2-bis(p-fluorophpheny-l)acetamide;

with (1S)-1-methylamino-1-(p-methylphenyl)-2-((3S)-3hydroxypyrrolidino)ethane:

N-methyl-N-[(1S)-1-(p-methylphenyl)-2-((3S)-3-hydroxypyrrolidino)ethyl]-2,2-bis(p-fluorophenyl)acetamide;

with (1S)-1-methylamino-1-(p-aminophenyl)-2-((3S)-3-hydroxypyrrolidino)ethane:

N-methyl-N-[(1S)-1-(p-aminophenyl)-2-((3S)-3-hydroxypyrrolidino)ethyl]-2,2-bis(p-fluorophenyl)acetamide;

with (1S)-1-methylamino-1-(p-fluorophenyl)-2-((3S)-3-hydroxypyrrolidino)ethane:
  N-methyl-N-[(1S)-1-(p-fluorophenyl)-2-((3S)-3-hydroxypyrrolidino)ethyl]-2,2-bis(p-fluorophenyl)acetamide;
with (1S)-1-methylamino-1-(2,4-difluorophenyl)-2-((3S)-3-hydroxypyrrolidino)ethane:
  N-methyl-N-[(1S)-1-(2,4-difluorophenyl)-2-((3S)-3hydroxypyrrolidino)ethyl]-2,2-bis(p-fluorophenyl)acetamide.

Example 3

The following are obtained in analogy to Example 1 by reaction of bis(p-chlorophenyl)acetic acid with (1S)-1-methylamino-1-phenyl-2-((3S)-3-hydroxypyrrolidino)ethane:
  N-methyl-N-[(1S)-1-phenyl-2-((3S)-3-hydroxypyrrolidino)ethyl]-2,2-bis(p-chlorophenyl)acetamide;
with (1S)-1-methylamino-1-(p-methoxyphenyl)-2-((3S)-3-hydroxypyrrolidino)ethane:
  N-methyl-N-[(1S)-1-(p-methoxyphenyl)-2-((3S)-3-hydroxypyrrolidino)ethyl]-2,2-bis(p-chlorophenyl)acetamide;
with (1S)-1-methylamino-1-phenyl-2-pyrrolidinoethane:
  N-methyl-N-[(1S)-1-phenyl-2-pyrrolidinoethyl]-2,2-bis(p-chlorophenyl)acetamide;
with (1S)-1-methylamino-1-(p-methoxyphenyl)-2-((3S)-3-hydroxypyrrolidino)ethane:
  N-methyl-N-[(1S)-1-(p-methoxyphenyl)-2-((3S)-3-hydroxypyrrolidino)ethyl]-2,2-bis(p-chlorophenyl)acetamide;
with 1-(pyrrolidinomethyl)-1,2,3,4-tetrahydroisoquinoline:
  2-[bis(p-chlorophenyl)acetyl]-1-(pyrrolidinomethyl)-1,2,3,4-tetrahydroisoquinoline;
with 2-(pyrrolidinomethyl)pyrrolidine:
  (2S)-1-bis(p-chlorophenyl)acetyl-2-(pyrrolidinomethyl)pyrrolidine;
with N-methyl-N-(2-pyrrolidino-4-methylpentyl)amine:
  N-methyl-N-(2-pyrrolidino-4-methylpentyl)-2,2-bis(p-chlorophenyl)acetamide;
with N-methyl-N-[2-((3S)-hydroxypyrrolidino)-4-methylpentyl]amine:
  N-methyl-N-[2-((3S)-hydroxypyrrolidino)-4-methylpentyl]-2,2-bis(p-chlorophenyl)acetamide;
with N-methyl-N-(2-pyrrolidino-3-methylbutyl)amine:
  N-methyl-N-(2-pyrrolidino-3-methylbutyl)-2,2-bis(p-chlorophenyl)acetamide;
with N-methyl-N-[2-((3S)-hydroxypyrrolidino)-3-methylbutyl]amine:
  N-methyl-N-[2-((3S)-hydroxypyrrolidino)-3-methylbutyl]-2,2-bis(p-chlorophenyl)acetamide;
with (1S)-1-methylamino-1-(p-hydroxyphenyl)-2-((3S)-3hydroxypyrrolidino)ethane:
  N-methyl-N-[(1S)-1-(p-hydroxyphenyl)-2-((3S)-3-hydroxypyrrolidino)ethyl]-2,2-bis(p-chlorophenyl)acetamide;
with (1S)-1-methylamino-1-(p-chlorophenyl)-2-pyrrolidinoethane:
  N-methyl-N-[(1S)-1-(p-chlorophenyl)-2-pyrrolidinoethyl]-2,2-bis(p-chlorophenyl)acetamide;
with (1S)-1-methylamino-1-(p-methoxyphenyl)-2-((3S)-3-hydroxypyrrolidino)ethane:
  N-methyl-N-[(1S)-1-(p-methoxyphenyl)-2-((3S)-3-hydroxypyrrolidino)ethyl]-2,2-bis(p-chlorophenyl)acetamide;
with 1-((3S)-3-hydroxypyrrolidinomethyl)-1,2,3,4-tetrahydroisoquinoline:
  2-[bis(p-chlorophenyl)acetyl]-1-((3S)-3-hydroxypyrrolidinomethyl)-1,2,3,4-tetrahydroisoquinoline;
with (1S)-1-methylamino-1-(2,4-dimethoxyphenyl)-2-((3S)-3-hydroxypyrrolidino)ethane:
  N-methyl-N-[(1S)-1-(2,4-dimethoxyphenyl)-2-((3S)-3-hydroxypyrrolidino)ethyl]-2,2-bis(p-chlorophenyl)acetamide;
with (1S)-1-methylamino-1-(2,4-dimethoxyphenyl)-2-pyrrolidinoethane:
  N-methyl-N-[(1S)-1-(2,4-dimethoxyphenyl)-2-pyrrolidinoethyl]-2,2-bis(p-chlorophenyl)acetamide;
with (1S)-1-methylamino-1-(p-trifluoromethylphenyl)-2-((3S)-3-hydroxypyrrolidino)ethane:
  N-methyl-N-[(1S)-1-(p-trifluoromethylphenyl)-2-((3S)-3-hydroxypyrrolidino)ethyl]-2,2-bis(p-chlorophphenyl)acetamide;
with (1S)-1-methylamino-1-(p-methylphenyl)-2-((3S)-3-hydroxypyrrolidino)ethane:
  N-methyl-N-[(1S)-1-(p-methylphenyl)-2-((3S)-3-hydroxypyrrolidino)ethyl]-2,2-bis(p-chlorophenyl)acetamide;
with (1S)-1-methylamino-1-(p-aminophenyl)-2-((3S)-3-hydroxypyrrolidino)ethane:
  N-methyl-N-[(1S)-1-(p-aminophenyl)-2-((3S)-3-hydroxypyrrolidino)ethyl]-2,2-bis(p-chlorophenyl)acetamide;
with (1S)-1-methylamino-1-(p-chlorophenyl)-2-((3S)-3-hydroxypyrrolidino)ethane:
  N-methyl-N-[(1S)-1-(p-chlorophenyl)-2-((3S)-3-hydroxypyrrolidino)ethyl]-2,2-bis(p-chlorophenyl)acetamide;
with (1S)-1-methylamino-1-(2,4-difluorophenyl)-2-((3S)-3-hydroxypyrrolidino)ethane:
  N-methyl-N-[(1S)-1-(2,4-difluorophenyl)-2-((3S)-3-hydroxypyrrolidino)ethyl]-2,2-bis(p-chlorophenyl)acetamide.

Example 4

30 ml of trimethylamine solution (33%) are added to a solution of 4.6 g of (1S)-1-methylamino-1-phenyl-2-((3S)-3-hydroxypyrrolidino)ethane [obtainable from (1S)-1-amino-1-phenyl-2-chloroethane by reaction with (3S)-3-hydroxypyrrolidine and subsequent methylation with methyl iodide] in 200 ml of dichloromethane. Then, while stirring, a solution of 1 equivalent of 9-fluorenecarbonyl chloride in 200 ml of dichloromethane is added dropwise, the mixture is stirred at room temperature for 2 hours, and the usual working up results in N-methyl-N-[(1S)-1-phenyl-2-((3S)-3-hydroxypyrrolidino)ethyl]-9-fluorenecarboxamide, Rf: 0.61.

The following are obtained analogously by reaction of 9-fluorenecarbonyl chloride
with (1S)-1-methylamino-1-phenyl-2-pyrrolidinoethane:
  N-methyl-N-[(1S)-1-phenyl-2-pyrrolidinoethyl]-9-fluorenecarboxamide, Rf: 0.67;
with 1-(pyrrolidinomethyl)-1,2,3,4-tetrahydroisoquinoline:
  2-(9-fluorenecarbonyl)-1-(pyrrolidinomethyl)-1,2,3,4-tetrahydroisoquinoline, Rf: 0.77;
with (1S)-1-methylamino-1-(p-methoxyphenyl)-2-((3S)-3-hydroxypyrrolidino)ethane:
  N-methyl-N-[(1S)-1-(p-methoxyphenyl)-2-((3S)-3-hydroxypyrrolidino)ethyl]-9-fluorenecarboxamide;

with (1S)-1-methylamino-1-(p-methylphenyl)-2-pyrrolidinoethane:
  N-methyl-N-[(1S)-1-(p-methylphenyl)-2-pyrrolidinoethyl]-9-fluorenecarboxamide;
with (1S)-1-methylamino-1-(p-ethoxyphenyl)-2-((3S)-3-hydroxypyrrolidino)ethane:
  N-methyl-N-[(1S)-1-(p-ethoxyphenyl)-2-((3S)-3-hydroxypyrrolidino)ethyl]-9-fluorenecarboxamide;
with 1-[(3S)-3-hydroxypyrrolidinomethyl]-1,2,3,4-tetrahydroisoquinoline:
  2-(9-fluorenecarbonyl)-1-[(3S)-3-hydroxypyrrolidinomethyl]-1,2,3,4-tetrahydroisoquinoline;
with (2S)-2-(pyrrolidinomethyl)pyrrolidine:
  (2S)-1-(9-fluorenecarbonyl)-2-(pyrrolidinomethyl)-pyrrolidine;
with N-methyl-N-(2-pyrrolidino-4-methylpentyl)amine:
  N-methyl-N-(2-pyrrolidino-4-methylpentyl)-9-fluorenecarboxamide;
with N-methyl-N-[2-((3S)-hydroxypyrrolidino)-4-methylpentyl]amine:
  N-methyl-N-[2-((3S)-hydroxypyrrolidino)-4-methylpentyl]-9-fluorenecarboxamide;
with N-methyl-N-(2-pyrrolidino-3-methylbutyl)amine:
  N-methyl-N-(2-pyrrolidino-3-methylbutyl)-9-fluorenecarboxamide;
with N-methyl-N-[2-((3S)-hydroxypyrrolidino)-3-methylbutyl]amine:
  N-methyl-N-[2-((3S)-hydroxypyrrolidino)-3-methylbutyl]-9-fluorenecarboxamide;
with (1S)-1-methylamino-1-(p-hydroxyphenyl)-2-((3S)-3-hydroxypyrrolidino)ethane:
  N-methyl-N-[(1S)-1-(p-hydroxyphenyl)-2-((3S)-3-hydroxypyrrolidino)ethyl]-9-fluorenecarboxamide;
with (1S)-1-methylamino-1-(p-chlorophenyl)-2-pyrrolidinoethane:
  N-methyl-N-[(1S)-1-(p-chlorophenyl)-2-pyrrolidinoethyl]-9-fluorenecarboxamide;
with (1S)-1-methylamino-1-(p-methoxyphenyl)-2-((3S)-3hydroxypyrrolidino)ethane:
  N-methyl-N-[(1S)-1-(p-methoxyphenyl)-2-((3S)-3-hydroxypyrrolidino)ethyl]-9-fluorenecarboxamide;
with (1S)-1-methylamino-1-(2,4-dimethoxyphenyl)-2-((3S)-3-hydroxypyrrolidino)ethane:
  N-methyl-N-[(1S)-1-(2,4-dimethoxyphenyl)-2-((3S)-3-hydroxypyrrolidino)ethyl]-9-fluorenecarboxamide;
with (1S)-1-methylamino-1-(2,4-dimethoxyphenyl)-2-pyrrolidinoethane:
  N-methyl-N-[(1S)-1-(2,4-dimethoxyphenyl)-2-pyrrolidinoethyl]-9-fluorenecarboxamide;
with (1S)-1-methylamino-1-(p-trifluoromethylphenyl)-2-((3S)-3-hydroxypyrrolidino)ethane:
  N-methyl-N-[(1S)-1-(p-trifluoromethylphenyl)-2-((3S)-3-hydroxypyrrolidino)ethyl]-9-fluorenecarboxamide;
with (1S)-1-methylamino-1-(p-methylphenyl)-2-((3S)-3-hydroxypyrrolidino)ethane:
  N-methyl-N-[(1S)-1-(p-methylphenyl)-2-((3S)-3-hydroxypyrrolidino)ethyl]-9-fluorenecarboxamide;
with (1S)-1-methylamino-1-(p-aminophenyl)-2-((3S)-3-hydroxypyrrolidino)ethane:
  N-methyl-N-[(1S)-1-(p-aminophenyl)-2-((3S)-3-hydroxypyrrolidino)ethyl]-9-fluorenecarboxamide;
with (1S)-1-methylamino-1-(p-fluorophenyl)-2-((3S)-3-hydroxypyrrolidino)ethane:
  N-methyl-N-[(1S)-1-(p-fluorophenyl)-2-((3S)-3-hydroxypyrrolidino)-ethyl]-9-fluorenecarboxamide;
with (1S)-1-methylamino-1-(2,4-difluorophenyl)-2-((3S)-3-hydroxypyrrolidino)ethane:
  N-methyl-N-[(1S)-1-(2,4-difluorophenyl)-2-((3S)-3-hydroxypyrrolidino)ethyl]-9-fluorenecarboxamide.

Example 5

The following are obtained in analogy to Example 4 by reaction of 9-xanthenecarbonyl chloride
with (1S)-1-methylamino-1-phenyl-2-pyrrolidinoethane:
  N-methyl-N-[(1S)-1-phenyl-2-pyrrolidinoethyl]-9-xanthenecarboxamide, Rf: 0.77;
with (1S)-1-methylamino-1-phenyl-2-((3S)-3-hydroxypyrrolidino)ethane:
  N-methyl-N-[(1S)-1-phenyl-2-((3S)-3-hydroxypyrrolidino)ethyl]-9-xanthenecarboxamide, Rf: 0.64;
with 1-(pyrrolidinomethyl)-1,2,3,4-tetrahydroisoquinoline:
  2-(9-xanthenecarbonyl)-1-(pyrrolidinomethyl)-1,2,3,4-tetrahydroisoquinoline;
with (1S)-1-methylamino-1-(p-methoxyphenyl)-2-((3S)-3hydroxypyrrolidino)ethane:
  N-methyl-N-[(1S)-1-(p-methoxyphenyl)-2-((3S)-3-hydroxypyrrolidino)ethyl]-9-xanthenecarboxamide;
with (1S)-1-methylamino-1-(p-methylphenyl)-2-pyrrolidinoethane:
  N-methyl-N-[(1S)-1-(p-methylphenyl)-2-pyrrolidinoethyl]-9-xanthenecarboxamide;
with (1S)-1-methylamino-1-(p-ethoxyphenyl)-2-((3S)-3-hydroxypyrrolidino)ethane:
  N-methyl-N-[(1S)-1-(p-ethoxyphenyl)-2-((3S)-3-hydroxypyrrolidino)ethyl]-9-xanthenecarboxamide;
with 1-[(3S)-3-hydroxypyrrolidinomethyl]-1,2,3,4-tetrahydroisoquinoline:
  2-(9-xanthenecarbonyl)-1-[(3S)-3-hydroxypyrrolidinomethyl]-1,2,3,4-tetrahydroisoquinoline;
with 1-(pyrrolidinomethyl)-1,2,3,4-tetrahydroisoquinoline:
  2-(9-xanthenecarbonyl)-1-(pyrrolidinomethyl)-1,2,3,4-tetrahydroisoquinoline, Rf: 0.76;
with (2S)-2-(pyrrolidinomethyl)pyrrolidine:
  (2S)-1-(9-xanthenecarbonyl)-2-(pyrrolidinomethyl)pyrrolidine;
with N-methyl-N-(2-pyrrolidino-4-methylpentyl)amine:
  N-methyl-N-(2-pyrrolidino-4-methylpentyl)-9-xanthenecarboxamide;
with N-methyl-N-[2-((3S)-hydroxypyrrolidino)-4-methylpentyl]amine;
  N-methyl-N-[2-((3S)-hydroxypyrrolidino)-4-methylpentyl]-9-xanthenecarboxamide;
with N-methyl-N-(2-pyrrolidino-3-methylbutyl)amine:
  N-methyl-N-(2-pyrrolidino-3-methylbutyl)-9-xanthenecarboxamide;
with N-methyl-N-[2-((3S)-hydroxypyrrolidino)-3-methylbutyl]amine:
  N-methyl-N-[2-((3S)-hydroxypyrrolidino)-3-methylbutyl]-9-xanthenecarboxamide;
with (1S)-1-methylamino-1-(p-hydroxyphenyl)-2-((3S)-3-hydroxypyrrolidinoethane:
  N-methyl-N-[(1S)-1-(p-hydroxyphenyl)-2-((3S)-3-hydroxypyrrolidino)ethyl]-9-xanthenecarboxamide;
with (1S)-1-methylamino-1-(p-chlorophenyl)-2-pyrrolidinoethane:
  N-methyl-N-[(1S)-1-(p-chlorophenyl)-2-pyrrolidinoethyl]-9-xanthenecarboxamide;

with (1S)-1-methylamino-1-(p-methoxyphenyl)-2-((3S)-3-hydroxypyrrolidino)ethane:

N-methyl-N-[(1S)-1-(p-methoxyphenyl)-2-((3S)-3-hydroxypyrrolidino)ethyl]-9-xanthenecarboxamide;

with (1S)-1-methylamino-1-(2,4-dimethoxyphenyl)-2-((3S)-3-hydroxypyrrolidino)ethane:

N-methyl-N-[(1S)-1-(2,4-dimethoxyphenyl)-2-((3S)-3-hydroxypyrrolidino)ethyl]-9-xanthenecarboxmide;

with (1S)-1-methylamino-1-(2,4-dimethoxyphenyl)-2-pyrrolidinoethane:

N-methyl-N-[(1S)-1-(2,4-dimethoxyphenyl)-2-pyrrolidinoethyl]-9-xanthenecarboxamide;

with (1S)-1-methylamino-1-(p-trifluoromethylphenyl)-2-((3S)-3-hydroxypyrrolidino)ethane:

N-methyl-N-[(1S)-1-(p-trifluoromethylphenyl)-2-((3S)-3-hydroxypyrrolidino)ethyl]-9-xanthenecarboxamide;

with (1S)-1-methylamino-1-(p-methylphenyl)-2-((3S)-3-hydroxypyrrolidino)ethane:

N-methyl-N-[(1S)-1-(p-methylphenyl)-2-((3S)-3-hydroxypyrrolidino)ethyl]-9-xanthenecarboxamide;

with (1S)-1-methylamino-1-(p-aminophenyl)-2-((3S)-3hydroxypyrrolidino)ethane:

N-methyl-N-[(1S)-1-(p-aminophenyl)-2-((3S)-3-hydroxypyrrolidino)ethyl]-9-xanthenecarboxamide;

with (1S)-1-methylamino-1-(p-fluorophenyl)-2-((3S)-3-hydroxypyrrolidino)ethane:

N-methyl-N-[(1S)-1-(p-fluorophenyl)-2-((3S)-3-hydroxypyrrolidino)ethyl]-9-xanthenecarboxamide;

with (1S)-1-methylamino-1-(2,4-difluorophenyl)-2-((3S)-3-hydroxypyrrolidino)ethane:

N-methyl-N-[(1S)-1-(2,4-difluorophenyl)-2-((3S)-3-hydroxypyrrolidino)ethyl]-9-xanthenecarboxamide.

Example 6

The following are obtained in analogy to Example 1 by reaction of 2,2-diphenylpropionyl chloride with (1S)-1-methylamino-1-(p-methoxyphenyl)-2-((3S)-3-hydroxypyrrolidino)ethane:

N-methyl-N-[(1S)-1-(p-methoxyphenyl)-2-((3S)-3-hydroxypyrrolidino)ethyl]-2,2-diphenylpropionamide;

with (1S)-1-methylamino-1-phenyl-2-pyrrolidinoethane:

N-methyl-N-[(1S)-1-phenyl-2-pyrrolidinoethyl]-2,2-diphenylpropionamide;

with (1S)-1-methylamino-1-(p-methoxyphenyl)-2-((3S)-3-hydroxypyrrolidino)ethane:

N-methyl-N-[(1S)-1-(p-methoxyphenyl)-2-((3S)-3-hydroxypyrrolidino)ethyl]-2,2-diphenylpropionamide;

with 1-(pyrrolidinomethyl)-1,2,3,4-tetrahydroisoquinoline:

2-(2,2-diphenylpropionyl)-1-(pyrrolidinomethyl)-1,2,3,4-tetrahydroisoquinoline, Rf: 0.65;

with 2-(pyrrolidinomethyl)pyrrolidine:

(2S)-1-(2,2-diphenylpropionyl)-2-(pyrrolidinomethyl)pyrrolidine;

with N-methyl-N-(2-pyrrolidino-4-methylpentyl)amine:

N-methyl-N-(2-pyrrolidino-4-methylpentyl)-2,2-diphenylpropionamide;

with N-methyl-N-[2-((3S)-hydroxypyrrolidino)-4-methylpentyl]amine:

N-methyl-N-[2-((3S)-hydroxypyrrolidino)-4-methylpentyl]-2,2-diphenylpropionamide;

with N-methyl-N-(2-pyrrolidino-3-methylbutyl)amine:

N-methyl-N-(2-pyrrolidino-3-methylbutyl)-2,2-diphenylpropionamide;

with N-methyl-N-[2-((3S)-hydroxypyrrolidino)-3-methylbutyl]amine:

N-methyl-N-[2-((3S)-hydroxypyrrolidino)-3-methylbutyl]-2,2-diphenylpropionamide;

with (1S)-1-methylamino-1-(p-hydroxyphenyl)-2-((3S)-3-hydroxypyrrolidino)ethane:

N-methyl-N-[(b 1S)-1-(p-hydroxyphenyl)-2-((3S)-3-hydroxypyrrolidino)ethyl]-2,2-diphenylpropionamide;

with (1S)-1-methylamino-1-(p-chlorophenyl)-2-pyrrolidinoethane:

N-methyl-N-[(1S)-1-(p-chlorophenyl)-2-pyrrolidinoethyl]-2,2-diphenylpropionamide;

with (1S)-1-methylamino-1-(p-methoxyphenyl)-2-((3S)-3-hydroxypyrrolidino)ethane:

N-methyl-N-[(1S)-1-(p-methoxyphenyl)-2-((3S)-3-hydroxypyrrolidino)ethyl]-2,2-diphenylpropionamide;

with 1-((3S)-3-hydroxypyrrolidinomethyl)-1,2,3,4-tetrahydroisoquinoline:

2-(2,2-diphenylpropionyl)-1-((3S)-3-hydroxypyrrolidinomethyl)-1,2,3,4-tetrahydroisoquinoline;

with (1S)-1-methylamino-1-(2,4-dimethoxyphenyl)-2-((3S)-3-hydroxypyrrolidino)ethane:

N-methyl-N-[(1S)-1-(2,4-dimethoxyphenyl)-2-((3S)-3-hydroxypyrrolidino)ethyl]-2,2-diphenylpropionamide;

with (1S)-1-methylamino-1-(2,4-dimethoxyphenyl)-2-pyrrolidinoethane:

N-methyl-N-[(1S)-1-(2,4-dimethoxyphenyl)-2-pyrrolidinoethyl]-2,2-diphenylpropionamide;

with (1S)-1-methylamino-1-(p-trifluoromethylphenyl)-2-((3S)-3-hydroxypyrrolidino)ethane:

N-methyl-N-[(1S)-1-(p-trifluoromethylphenyl)-2-((3S)-3-hydroxypyrrolidino)ethyl]-2,2-diphenylpropionamide;

with (1S)-1-methylamino-1-(p-methylphenyl)-2-((3S)-3-hydroxypyrrolidino)ethane:

N-methyl-N-[(1S)-1-(p-methylphenyl)-2-((3S)-3-hydroxypyrrolidino)ethyl]2,2-diphenylpropionamide;

with (1S)-1-methylamino-1-(p-aminophenyl)-2-((3S)-3-hydroxypyrrolidino)ethane:

N-methyl-N-[(1S)-1-(p-aminophenyl)-2-((3S)-3-hydroxypyrrolidino)ethyl]-2,2-diphenylpropionamide;

with (1S)-1-methylamino-1-(p-fluorophenyl)-2-((3S)-3-hydroxypyrrolidino)ethane:

N-methyl-N-[(1S)-1-(p-fluorophenyl)-2-((3S)-3-hydroxypyrrolidino)ethyl]-2,2-diphenylpropionamide;

with (1S)-1-methylamino-1-(2,4-difluorophenyl)-2-((3S)-3-hydroxypyrrolidino)ethane:

N-methyl-N-[(1S)-1-(2,4-difluorophenyl)-2-((3S)-3-hydroxypyrrolidino)ethyl]-2,2-diphenylpropionamide.

Example 7

The following are obtained in analogy to Example 1 by reaction of 2,2-bis(p-fluorophenyl)propionic acid
with (1S)-1-methylamino-1-phenyl-2-((3S)-3-hydroxypyrrolidino)ethane:

N-methyl-N-[(1S)-1-phenyl-2-((3S)-3-hydroxypyrrolidino)ethyl]-2,2-bis(p-fluorophenyl)propionamide;

with (1S)-1-methylamino-1-(p-methoxyphenyl)-2-((3S)-3-hydroxypyrrolidino)ethane:

N-methyl-N-[(1S)-1-(p-methoxyphenyl)-2-((3S)-3-hydroxypyrrolidino)ethyl]-2,2-bis(p-fluorophenyl)propionamide;

with (1S)-1-methylamino-1-phenyl-2-pyrrolidinoethane:

N-methyl-N-[(1S)-1-phenyl-2-pyrrolidinoethyl]-2,2-bis(p-fluorophenyl)propionamide;

with (1S)-1-methylamino-1-(p-methoxyphenyl)-2-((3S)-3-hydroxypyrrolidino)ethane:

N-methyl-N-[(1S)-1-(p-methoxyphenyl)-2-((3S)-3-hydroxypyrrolidino)ethyl]-2,2-bis(p-fluorophenyl)propionamide;

with 1-(pyrrolidinomethyl)-1,2,3,4-tetrahydroisoquinoline:

2-[2,2-bis(p-fluorophenyl)propionyl]-1-(pyrrolidinomethyl)-1,2,3,4-tetrahydroisoquinoline;

with N-methyl-N-(2-pyrrolidino-4-methylpentyl)amine:

N-methyl-N-(2-pyrrolidino-4-methylpentyl)-2,2-bis-(p-fluorophenyl)propionamide;

with N-methyl-N-[2-((3S)-hydroxypyrrolidino)-4-methylpentyl]amine;

N-methyl-N-[2-((3S)-hydroxypyrrolidino)-4-methylpentyl]-2,2-bis(p-fluorophenyl)propionamide;

with N-methyl-N-[2-((3S)-hydroxypyrrolidino)-3-methylbutyl]amine:

N-methyl-N-[2-((3S)-hydroxypyrrolidino)-3-methylbutyl]-2,2-bis(p-fluorophenyl)propionamide;

with (1S)-1-methylamino-1-(p-fluorophenyl)-2-((3S)-3-hydroxypyrrolidino)ethane:

N-methyl-N-[(1S)-1-(p-fluorophenyl)-2-((3S)-3-hydroxypyrrolidino)ethyl]-2,2-bis(p-fluorophenyl)propionamide;

with (1S)-1-methylamino-1-(2,4-difluorophenyl)-2-((3S)-3-hydroxypyrrolidino)ethane:

N-methyl-N-[(1S)-1-(2,4-difluorophenyl)-2-((3S)-3-hydroxypyrrolidino)ethyl]-2,2-bis(p-fluorophenyl)propionamide.

Example 8

The following are obtained in analogy to Example 1 by reaction of 2,2-bis(p-chlorophenyl)propionyl chloride with (1S)-1-methylamino-1-phenyl-2-((3S)-3-hydroxypyrrolidino)ethane:

N-methyl-N-[(1S)-1-phenyl-2-((3S)-3-hydroxypyrrolidino)ethyl]-2,2-di(p-chlorophenyl)propionamide;

with (1S)-1-methylamino-1-(p-methoxyphenyl)-2-((3S)-3-hydroxypyrrolidino)ethane:

N-methyl-N-[(1S)-1-(p-methoxyphenyl)-2-((3S)-3-hydroxypyrrolidino)ethyl]-2,2-di(p-chlorophenyl)propionamide;

with (1S)-1-methylamino-1-phenyl-2-pyrrolidinoethane:

N-methyl-N-[(1S)-1-phenyl-2-pyrrolidinoethyl]-2,2-di(p-chlorophenyl)propionamide;

with (1S)-1-methylamino-1-(p-methoxyphenyl)-2-((3S)-3-hydroxypyrrolidino)ethane:

N-methyl-N-[(1S)-1-(p-methoxyphenyl)-2-((3S)-3-hydroxypyrrolidino)ethyl]-2,2-di-(p-chlorophenyl)propionamide;

with N-methyl-N-[2-((3S)-hydroxypyrrolidino)-3-methylbutyl]amine:

N-methyl-N-[2-((3S)-hydroxypyrrolidino)-3-methylbutyl]-2,2-bis(p-chlorophenyl)propionamide;

with (1S)-1-methylamino-1-(p-hydroxyphenyl)-2-((3S)-3-hydroxypyrrolidino)ethane:

N-methyl-N-[(1S)-1-(p-hydroxyphenyl)-2-((3S)-3-hydroxypyrrolidino)ethyl]-2,2-bis(p-chlorophenyl)propionamide;

with (1S)-1-methylamino-1-(p-aminophenyl)-2-((3S)-3-hydroxypyrrolidino)ethane:

N-methyl-N-[(1S)-1-(p-aminophenyl)-2-((3S)-3-hydroxypyrrolidino)ethyl]-2,2-bis(p-chlorophenyl)propionamide;

with (1S)-1-methylamino-1-(p-chlorophenyl)-2-((3S)-3-hydroxypyrrolidino)ethane:

N-methyl-N-[(1S)-1-(p-chlorophenyl)-2-((3S)-3-hydroxypyrrolidino)ethyl]-2,2-bis(p-chlorophenyl)propionamide;

with (1S)-1-methylamino-1-(2,4-difluorophenyl)-2-((3S)-3-hydroxypyrrolidino)ethane:

N-methyl-N-[(1S)-1-(2,4-difluorophenyl)-2-((3S)-3-hydroxypyrrolidino)ethyl]-2,2-bis(p-chlorophenyl)propionamide. propionamide.

Example 9

4.3 g of bis(p-chlorophenyl)acetic hydrazide [for example obtainable from the corresponding ethyl ester by reaction with hydrazine] are dissolved in 200 ml of very dilute hydrochloric acid and, while stirring at 0°, a solution of 2.0 g of NaNO$_2$ in 40 ml of water is added dropwise, the mixture is stirred for 30 min., and the azide which has formed is extracted with dichloromethane. The reagent obtained after drying over MgSO$_4$ and concentration to 50 ml is added dropwise to a solution of (1S)-1-methylamino-1-(p-methoxyphenyl)-2-((3)-3-hydroxypyrrolidino)ethane and 4 ml of triethylamine in 100 ml of dichloromethane. The mixture is stirred at 20° for 2 hours, and the usual working up results in N-methyl-N[(1S)-1-(P-methoxyphenyl)-2-((3S)-3-hydroxypyrrolino)-ethyl]-2,2-bis(p-chlorophenyl)acetamide.

Example 10

A solution of 1 g of N-methyl-N-[(1S)-1-(p-benzyloxyphenyl)-2-((3S)-3-hydroxypyrrolidino)ethyl]-2,2-diphenylacetamide in 25 ml of ethyl acetate is hydrogenated on 0.5 g of 5% Pd-C at 20° and under 1 bar until hydrogen uptake ceases, the mixture is filtered, the filtrate is evaporated, and N-methyl-N-[(1S)-1-(p-hydroxyphenyl)-2-((3S)-3-hydroxypyrrolidino)ethyl]-2,2-diphenylacetamide is obtained.

The following are obtained analogously from the corresponding o- and m-benzyloxy derivatives:

N-methyl-N-[(1S)-1-(o-hydroxyphenyl)-2-((3S)-3-hydroxypyrrolidino)ethyl]-2,2-diphenylacetamide;

N-methyl-N-[(1S)-1-(m-hydroxyphenyl)-2-((3S)-3-hydroxypyrrolidino)ethyl]-2,2-diphenylacetamide;

N-methyl-N-[(1S)-1-(o-hydroxyphenyl)-2-pyrrolidinoethyl]-2,2-diphenylacetamide;

N-methyl-N-[(1S)-1-(m-hydroxyphenyl)-2-pyrrolidinoethyl]-2,2-diphenylacetamide;

N-methyl-N-[(1S)-1-(o-hydroxyphenyl)-2-pyrrolidinoethyl]-2,2-bis(p-chlorophenyl)acetamide;

N-methyl-N-[(1S)-1-(m-hydroxyphenyl)-2-pyrrolidinoethyl]-2,2-bis(p-chlorophenyl)acetamide;

N-methyl-N-[(1S)-1-(o-hydroxyphenyl)-2-pyrrolidinoethyl]-2,2-bis(p-fluorophenyl)acetamide;

N-methyl-N-[(1S)-1-(m-hydroxyphenyl)-2-pyrrolidinoethyl]-2,2-bis(p-fluorophenyl)acetamide.

The following are obtained analogously from the corresponding p-benzyloxy derivatives:

N-methyl-N-[(1S)-1-(p-hydroxyphenyl)-2-pyrrolidinoethyl]-2,2-diphenylacetamide;

N-methyl-N-[(1S)-1-(p-hydroxyphenyl)-2-pyrrolidinoethyl]-2,2-bis(p-chlorophenyl)acetamide;

N-methyl-N-[(1S)-1-(p-hydroxyphenyl)-2-pyrrolidinoethyl]-2,2-bis(p-fluorophenyl)acetamide.

Example 11

3.2 g of N-[(1S)-1-phenyl-2-((3S)-3-hydroxypyrrolidino)ethyl]-2,2-diphenylacetamide are dissolved in 150 ml of dichloromethane and, while stirring, 1 equivalent of methyl iodide dissolved in 10 ml of dichloromethane is added dropwise, the solution is concentrated, and the usual working up results in N-methyl-N-[(1S)-1-phenyl-2-((3S)-3-hydroxypyrrolidino)ethyl]-2,2-diphenylacetamide, Rf: 0.60.

The following are obtained analogously by reaction with methyl iodide
from
N-[(1S)-1-(p-methoxyphenyl)-2-((3S)-3-hydroxypyrrolidino)ethyl]-2,2-diphenylacetamide: N-methyl-N-[(1S)-1-(p-methoxyphenyl)-2-((3S)-3-hydroxypyrrolidino)ethyl]-2,2-diphenylacetamide, Rf: 061;
from
N-[(1S)-1-phenyl-2-pyrrolidinoethyl]-2,2-diphenylacetamide: N-methyl-N-[(1S)-1-phenyl-2-pyrrolidinoethyl]-2,2-diphenylacetamide, Rf: 0.71;
from
N-[(1S)-1-(p-methoxyphenyl)-2-((3S)-3-hydroxypyrrolidino)ethyl]-2,2-diphenylacetamide: N-methyl-N-[(1S)-1-(p-methoxyphenyl)-2-((3S)-3-hydroxypyrrolidino)ethyl]-2,2 -diphenylacetamide, Rf: 0.61.

Example 12

The following is obtained in analogy to Example 10 by hydrogenation of N-methyl-N-[(1S)-1-phenyl-2-((3S)-3-hydroxypyrrolidino)ethyl]-2,2-diphenyl-2-benzyloxyacetamide:

N-methyl-N-[(1S)-1-phenyl-2-((3S)-3-hydroxypyrrolidino)ethyl]-2,2-diphenyl-2-hydroxyacetamide.

The following are obtained analogously by hydrogenation of the corresponding 2,2-diphenyl-2-benzyloxyacetamides:

N-methyl-N-[(1S)-1-(p-methoxyphenyl)-2-((3S)-3-hydroxypyrrolidino)ethyl]-2,2-diphenyl-2-hydroxyacetamide;

N-methyl-N-[(1S)-1-phenyl-2-pyrrolidinoethyl]-2,2-diphenyl-2-hydroxyacetamide;

N-methyl-N-[(1S)-1-(p-methoxyphenyl)-2-((3S)-3-hydroxypyrrolidino)ethyl]-2,2-diphenyl-2-hydroxyacetamide;

N-methyl-N-(2-pyrrolidino-4-methylpentyl)-2,2-diphenyl-2-hydroxyacetamide;

N-methyl-N-[2-((3S)-hydroxypyrrolidino)-4-methylpentyl]-2,2-diphenyl-2-hydroxyacetamide;

N-methyl-N-(2-pyrrolidino-3-methylbutyl)-2,2-diphenyl-2-hydroxyacetamide;

N-methyl-N-[2-((3S)-hydroxypyrrolidino)-3-methylbutyl]-2,2-diphenyl-2-hydroxyacetamide;

N-methyl-N-[(1S)-1-(p-hydroxyphenyl)-2-((3S)-3-hydroxypyrrolidino)ethyl]-2,2-diphenyl-2-hydroxyacetamide;

N-methyl-N-[(1S)-1-(p-chlorophenyl)-2-pyrrolidinoethyl]-2,2-diphenyl-2-hydroxyacetamide;

N-methyl-N-[(1S)-1-(p-methoxyphenyl)-2-((3S)-3-hydroxypyrrolidino)ethyl]-2,2-diphenyl-2-hydroxyacetamide;

N-methyl-N-[(1S)-1-(2,4-dimethoxyphenyl)-2-((3S)-3hydroxypyrrolidino)ethyl]-2,2-diphenyl-2-hydroxyacetamide;

N-methyl-N-[(1S)-1-(2,4-dimethoxyphenyl)-2-pyrrolidinoethyl]-2,2-diphenyl-2-hydroxyacetamide.

The following examples relate to pharmaceutical preparations.

Example A: Vials

A solution of 100 g of N-methyl-N-[1-phenyl-2-(3-hydroxypyrrolidino)ethyl]diphenylacetamide and 5 g of disodium hydrogen phosphate in 3 l of double distilled water is adjusted to pH 6.5 with 2N hydrochloric acid, filtered sterile, dispensed into vials, lyophilized under sterile conditions and sealed sterile. Each vial contains 5 mg of active substance.

Example B: Suppositories

A mixture of 20 g of 2-(2,2-diphenylpropionyl)-1-(1-pyrrolidinylmethyl)- 1,2,3,4-tetrahydroisoquinole with 100 g of soya lecithin and 1400 g of cocoa butter is melted, poured into molds and left to cool. Each suppository contains 20 mg of active substance.

Example C: Solution

A solution of 1 g of N-methyl-N-[(1S)-1-(4-methoxyphenyl)-2-((3S)-3-hydroxypyrrolidino) ethyl]2,2-diphenylacetamide, 9.38 g of $NaH_2PO_4.2 H_2O$, 28.48 g of $Na_2HPO_4.12 H_2O$ and 0.1 g of benzalconium chloride in 940 ml of double distilled water is prepared. The pH is adjusted to 6.8, the volume is made up to 1 l, and the solution is sterilised by irradiation. This solution can be used in the form of eye drops.

Example D: Ointment 500 mg of N-methyl-N-[(1S)-1-phenyl-2-((3S)-3-hydroxypyrrolidino)ethyl]-2,2-diphenylacetamide are mixed with 99.5 g of petrolatum under aseptic conditions.

Example E: Tablets

A mixture of 1 kg of N-methyl-N-[(1S)-1-phenyl-2-((3S)-hydroxypyrrolidino)ethyl]-9-fluorenecarboxamide, 4 kg of lactose, 1.2 kg of potato starch, 0.2 kg of talc and 0.1 kg of magnesium stearate is compressed to tablets in a conventional way such that each tablet contains 10 mg of active substance.

Example F: Coated Tablets

Tablets are produced by compression in analogy to Example E and are then covered in a conventional way with a coating of sucrose, potato starch, talc, tragacanth and colorant.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An arylacetamide of the formula I

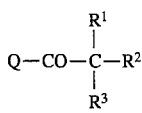

in which

Q is $R^4$—CH(CH$_2$Z)—NA—,

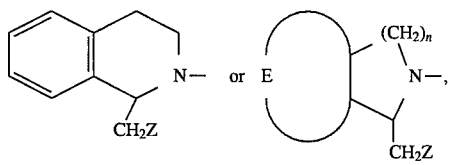

$R^1$ is Ar, cycloalkyl with 3–7 C atoms or $C_4$–$C_8$-cycloalkyl-$C_1$–$C_7$-alkyl, $R^2$ is Ar, $R^3$ is H, OH, OA or A, $R^4$ is A or phenyl which can optionally be substituted once or twice by F, Cl, Br, I, OH, OA, CF$_3$, NO$_2$, NH$_2$, NHA, NHCOA, NHSO$_2$A or NA$_2$, $R^5$ and $R^6$ are each, independently of one another, H, F, Cl, Br, I, OH, OA, CF$_3$, NH$_2$, NHA, NA$_2$, NHCOA, NHCONH$_2$, NO$_2$ or taken together are methylenedioxy, A is alkyl with 1–7 C atoms, Z is 1-pyrrolidinyl which can optionally be substituted once by OH, OA, O—COCH$_3$ or CH$_2$OH, Ar is a mono- or bicyclic aromatic radical which can optionally be substituted once, twice or three times by A, Hal, OH, OA, CF$_3$, NH$_2$, NHA, NA$_2$, NHCOA and/or NHCONH$_2$, and provided that when $R^4$ is not phenyl then Ar must be substituted at least once, or physiologically acceptable salts thereof.

2. An arylacetamide compound of claim 1 which is a) N-methyl-N-[1-phenyl-2-(3-hydroxypyrrolidino)ethyl]-2,2-diphenylacetamide;

b) N-methyl-N-[(1S)-1-(4-methoxyphenyl)-2-((3S)-3-hydroxypyrrolidino)ethyl]-2,2-diphenylacetamide;

c) N-methyl-N-[(1S)-1-phenyl-2-((3S)-3-hydroxypyrrolidino)ethyl]-2,2-diphenylacetamide;

d) N-methyl-N-[(1S)-1-phenyl-2-((3S)-hydroxypyrrolidino)ethyl]-9-fluorenecarboxamide;

e) N-methyl-N-[(1S)-1-phenyl-2-pyrrolidino)-ethyl]-2,2-di(4-fluorophenyl)acetamide;

f) N-methyl-N-[1-(2-methylpropyl)-2-pyrrolidino-ethyl]-2,2-diphenylacetamide; or g) N-methyl-N-[1-phenyl-2-(3-hydroxypyrrolidino)ethyl]-2,2-bis(4-fluorophenyl)acetamide.

3. A pharmaceutical preparation comprising at least one compound of claim 1.

4. A pharmaceutical preparation according to claim 3, which further comprises at least one physiologically acceptable solid, liquid or semiliquid vehicle or ancillary substance.

5. A method for treating inflammation-related hyperalgesia comprising administering a compound of claim 1.

6. A method for treating cerebral oedemas comprising administering a compound of claim 1.

7. A method for treating hypoxia comprising administering a compound of claim 1.

8. A method for treating pain comprising administering a compound of claim 1.

9. A method for controlling diseases selected from the group consisting of hypoxia, cerebral oedemas and inflammation-related hyperalgesia which comprises administering an effective amount of a compound of claim 1 or a physiologically acceptable salt thereof to a patient in need thereof.

10. An arylacetamide of claim 1, wherein Ar is unsubstituted phenyl, o-, m- or p-aminophenyl, o-, m- or p-hydroxyphenyl, o-, m- or p-acetamidophenyl, o-, m- or p-fluorophenyl, o-, m- or p-chlorophenyl, or o-, m- or p-trifluoromethylphenyl.

11. An arylacetamide of claim 1, wherein $R^1$ and $R^2$ are independently phenyl, p-fluorophenyl or p-chlorophenyl.

12. An arylacetamide of claim 1, wherein $R^4$ is phenyl, p-hydroxyphenyl, p-methoxyphenyl, p-F-, p-Cl- or p-trifluoromethylphenyl or A.

13. An arylacetamide of claim 1, wherein $R^5$ and $R^6$ are independently hydrogen, F, Cl, OH or methoxy.

14. An arylacetamide of claim 1, wherein $R^1$ and $R^2$ are both phenyl.

15. An arylacetamide of claim 1, wherein $R^1$ and $R^2$ are each p-fluorophenyl or p-chlorophenyl.

16. An arylacetamide of claim 1, wherein $R^1$ and $R^2$ are both phenyl and $R^3$ is hydrogen or methyl.

17. An arylacetamide of claim 1, wherein $R^1$ and $R^2$ are each p-fluorophenyl or p-chlorophenyl and $R^3$ is hydrogen.

18. An arylacetamide of claim 1, wherein $R^4$ is phenyl, p-hydroxyphenyl, p-methoxyphenyl, p-F-, p-Cl- or p-trifluoromethylphenyl.

19. An arylacetamide of claim 1, wherein Z is 1-pyrrolidinyl substituted once by OH, OA, O—COCH$_3$ or CH$_2$OH.

20. An arylacetamide of claim 1, wherein Z is 1-pyrrolidinyl substituted once by OH.

21. The arylacetamide of claim 1 which is N-methyl-N-[(1S)-1-phenyl-2-((3S)-3-hydroxypyrrolidino)ethyl]-2,2-diphenylacetamide.

22. An arylacetamide of claim 1, wherein $R^4$ is phenyl optionally substituted once or twice by F, Cl, Br, I, OH, OA, CF$_3$, NO$_2$, NH$_2$, NHA, NHCOA, NHSO$_2$A or NA$_2$.

* * * * *

UNITED STATES PATENT AND TRADEMARK OFFICE
CERTIFICATE OF CORRECTION

PATENT NO.   : 5,532,266
DATED        : July 2, 1996
INVENTOR(S)  : Gottschlich et al.

Page 1 of 1

It is certified that error appears in the above-identified patent and that said Letters Patent is hereby corrected as shown below:

Column 21,
Lines 8-14, delete " 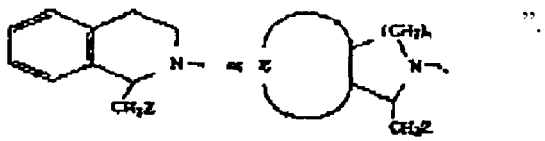 ".

Lines 23-26, delete "$R^5$ and $R^6$ are each, independently of one another H, F, Cl, Br, I, OH, OA, $CF_3$, $NH_2$, NHA, $NA_2$, NHCOA, $NHCONH_2$, $NO_2$ or taken together are methylenedioxy.".
Lines 44-45, delete "d) N-methyl-N-[(1S)-1-phenyl-2((3S)-3-hydroxypyrrolidino)ethyl]-9-fluorenecarboxamide.".

Column 22,
Lines 29-30, delete "13. An arylacetamide of claim 1, wherein $R^5$ and $R^6$ are independently hydrogen, F, Cl, OH or methoxy.".

Signed and Sealed this

Sixth Day of June, 2006

JON W. DUDAS
*Director of the United States Patent and Trademark Office*